(12) United States Patent
Goble

(10) Patent No.: US 7,717,910 B2
(45) Date of Patent: May 18, 2010

(54) ELECTROSURGICAL GENERATOR

(75) Inventor: Colin C. O. Goble, Surrey (GB)

(73) Assignee: Gyrus Medical Limited, Cardiff (GB)

( * ) Notice: Subject to any disclaimer, the term of this patent is extended or adjusted under 35 U.S.C. 154(b) by 371 days.

(21) Appl. No.: 11/727,327

(22) Filed: Mar. 26, 2007

(65) Prior Publication Data
US 2007/0173808 A1    Jul. 26, 2007

Related U.S. Application Data

(63) Continuation of application No. 10/743,095, filed on Dec. 23, 2003, now Pat. No. 7,211,081.

(60) Provisional application No. 60/449,859, filed on Feb. 27, 2003, provisional application No. 60/505,756, filed on Dec. 3, 2003.

(30) Foreign Application Priority Data

| Jan. 9, 2003 | (GB) | ................................. 0300508.9 |
| Jul. 29, 2003 | (GB) | ................................. 0317728.4 |

(51) Int. Cl.
*A61B 18/18* (2006.01)

(52) U.S. Cl. .............................. 606/34; 606/39; 606/46

(58) Field of Classification Search ............. 606/32–42; 607/100–105
See application file for complete search history.

(56) References Cited

U.S. PATENT DOCUMENTS

| 3,685,518 | A | 8/1972 | Beuerle et al. |
| 3,768,482 | A | 10/1973 | Shaw |
| 4,038,984 | A | 8/1977 | Sittner |
| 4,092,986 | A | 6/1978 | Schneiderman |
| 4,117,846 | A | 10/1978 | Williams |
| 4,188,927 | A | 2/1980 | Harris |
| 4,492,231 | A | 1/1985 | Auth |
| 4,517,976 | A | 5/1985 | Murakoshi et al. |

(Continued)

FOREIGN PATENT DOCUMENTS

EP    0 247 717 A2    12/1987

(Continued)

*Primary Examiner*—Michael Peffley
*Assistant Examiner*—Ronald Hupczey, Jr.
(74) *Attorney, Agent, or Firm*—Oliff & Berridge, PLC

(57) ABSTRACT

An electrosurgical generator for supplying RF power to an electrosurgical instrument for cutting or vaporizing tissue has an RF output stage (42) with an RF power bridge (Q1, Q2, Q3, Q4), a pair of output lines (74) and a series-resonant output network (48). The output impedance of the output stage (42) at the output lines (74) is less than $200/\sqrt{P}$ ohms, where P is the maximum continuous RF output power of the generator. The generator offers improved cutting and vaporizing performance, especially in relation to the reliability with which an arc can be struck when presented with an initial low impedance load. Overloading of the output stage is prevented by rapidly operating protection circuitry responsive to a predetermined electrical condition such as a substantial short-circuit across the output lines. In the preferred embodiment, the output stage is capable of maintaining output pulses at least 1 kW peak by supplying the power bridge from a large reservoir capacitor (60). Pulsing is dynamically variable in response to load conditions by controlling the maximum energy per pulse in response to the reservoir capacitor voltage.

14 Claims, 7 Drawing Sheets

U.S. PATENT DOCUMENTS

| | | | |
|---|---|---|---|
| 4,543,474 A | | 9/1985 | Horsma et al. |
| 4,590,934 A | * | 5/1986 | Malis et al. .................... 606/37 |
| 4,727,874 A | | 3/1988 | Bowers et al. |
| 5,067,953 A | * | 11/1991 | Feucht ......................... 606/34 |
| 5,122,137 A | | 6/1992 | Lennox |
| 5,134,356 A | | 7/1992 | El-Sharkawi et al. |
| 5,318,563 A | | 6/1994 | Malis et al. |
| 5,346,491 A | | 9/1994 | Oertli |
| 5,423,810 A | | 6/1995 | Goble et al. |
| 5,445,638 A | | 8/1995 | Rydell et al. |
| 5,451,224 A | | 9/1995 | Goble et al. |
| 5,496,312 A | | 3/1996 | Klicek |
| 5,496,313 A | | 3/1996 | Gentelia et al. |
| 5,628,771 A | | 5/1997 | Mizukawa et al. |
| 5,693,045 A | | 12/1997 | Eggers |
| 5,716,366 A | | 2/1998 | Yates |
| 5,720,744 A | | 2/1998 | Eggleston et al. |
| 5,757,445 A | | 5/1998 | Vu et al. |
| 5,766,153 A | | 6/1998 | Eggers et al. |
| 5,836,943 A | | 11/1998 | Miller, III |
| 5,885,281 A | | 3/1999 | Urueta |
| 5,931,836 A | | 8/1999 | Hatta et al. |
| 6,033,399 A | | 3/2000 | Gines |
| 6,074,386 A | * | 6/2000 | Goble et al. .................... 606/34 |
| 6,093,186 A | | 7/2000 | Goble |
| 6,106,524 A | | 8/2000 | Eggers et al. |
| 6,132,426 A | | 10/2000 | Kroll |
| 6,142,992 A | | 11/2000 | Cheng et al. |
| 6,228,080 B1 | | 5/2001 | Gines |
| 6,228,081 B1 | | 5/2001 | Goble |
| 6,235,020 B1 | * | 5/2001 | Cheng et al. .................... 606/34 |
| 6,296,636 B1 | | 10/2001 | Cheng et al. |
| 6,385,059 B1 | * | 5/2002 | Telefus et al. ............ 363/21.15 |
| 6,398,779 B1 | | 6/2002 | Buysse et al. |
| 6,413,255 B1 | | 7/2002 | Stern |
| 6,642,711 B2 | | 11/2003 | Kawate et al. |
| 6,679,269 B2 | | 1/2004 | Swanson |
| 6,802,843 B2 | | 10/2004 | Truckai et al. |
| 6,843,789 B2 | | 1/2005 | Goble |
| 6,855,142 B2 | | 2/2005 | Harano et al. |
| 6,893,435 B2 | | 5/2005 | Goble |
| 6,929,644 B2 | | 8/2005 | Truckai et al. |
| 7,066,933 B2 | | 6/2006 | Hagg |
| 7,083,619 B2 | | 8/2006 | Truckai et al. |
| 2002/0165530 A1 | * | 11/2002 | Harano et al. .................. 606/32 |
| 2003/0078573 A1 | | 4/2003 | Truckai et al. |
| 2004/0030329 A1 | * | 2/2004 | Hagg .......................... 606/38 |
| 2005/0177150 A1 | | 8/2005 | Amoah et al. |

FOREIGN PATENT DOCUMENTS

| | | |
|---|---|---|
| EP | 0 386 425 A2 | 9/1990 |
| EP | 0 517 243 A1 | 9/1992 |
| EP | 0 694 290 A2 | 1/1996 |
| EP | 0 754 437 A2 | 1/1997 |
| EP | 1 034 746 A2 | 9/2000 |
| EP | 1 053 719 A1 | 11/2000 |
| EP | 1 157 667 A2 | 11/2001 |
| EP | 1 053 720 A1 | 11/2002 |
| JP | A-07-500514 | 1/1995 |
| JP | A-09-173349 | 7/1997 |
| JP | A-2002-360712 | 12/2002 |
| WO | WO 92/22256 | 12/1992 |
| WO | WO 96/10950 | 4/1996 |
| WO | WO 96/14021 | 5/1996 |
| WO | WO 97/24073 A1 | 7/1997 |
| WO | WO 98/27880 A1 | 7/1998 |
| WO | WO 99/20213 | 4/1999 |
| WO | WO 00/54683 | 9/2000 |
| WO | WO 02/21992 A1 | 11/2000 |
| WO | WO 02/11634 | 2/2002 |
| WO | WO 02/36028 A1 | 5/2002 |
| WO | WO 02/53048 A1 | 7/2002 |

* cited by examiner

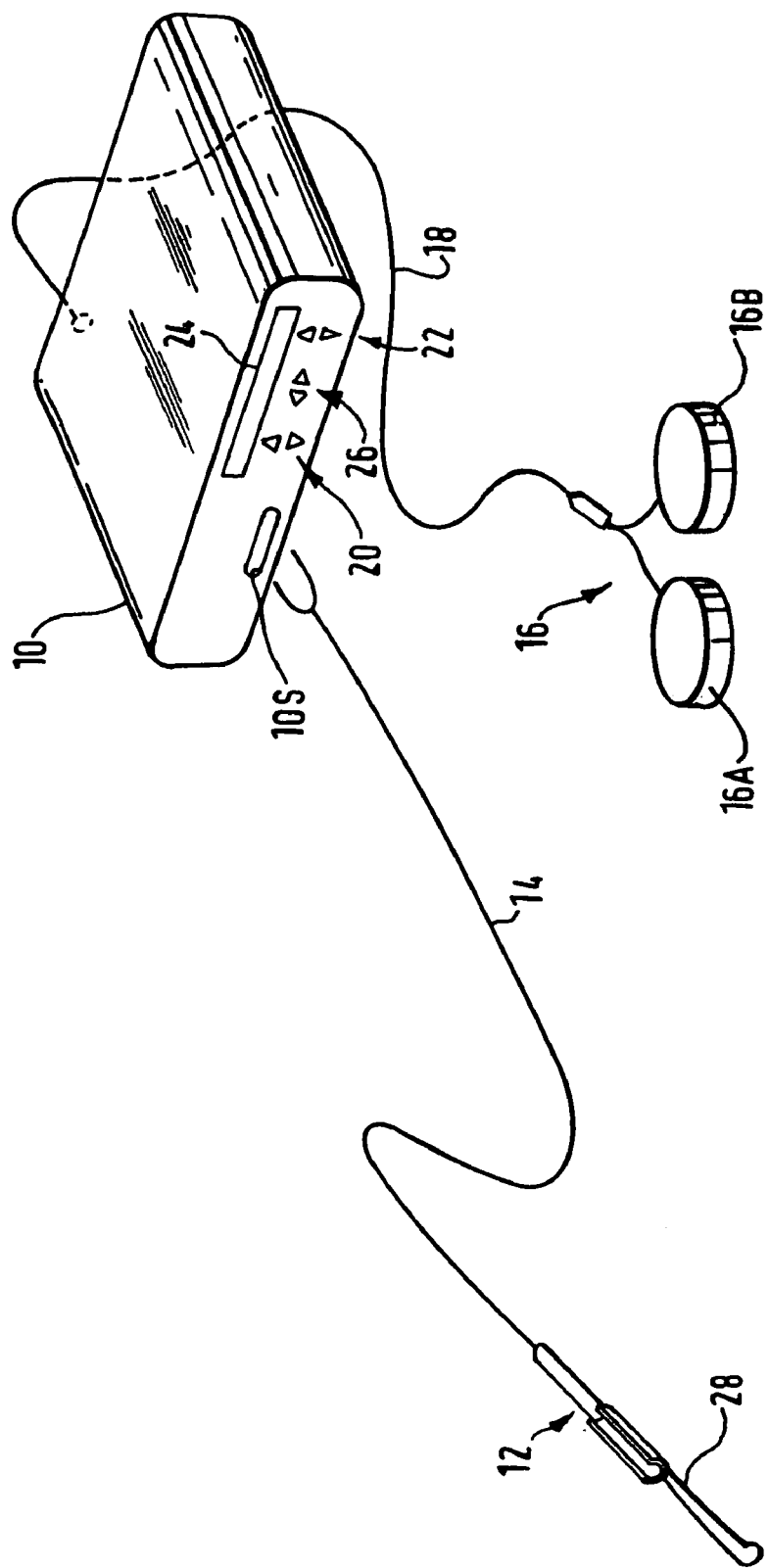

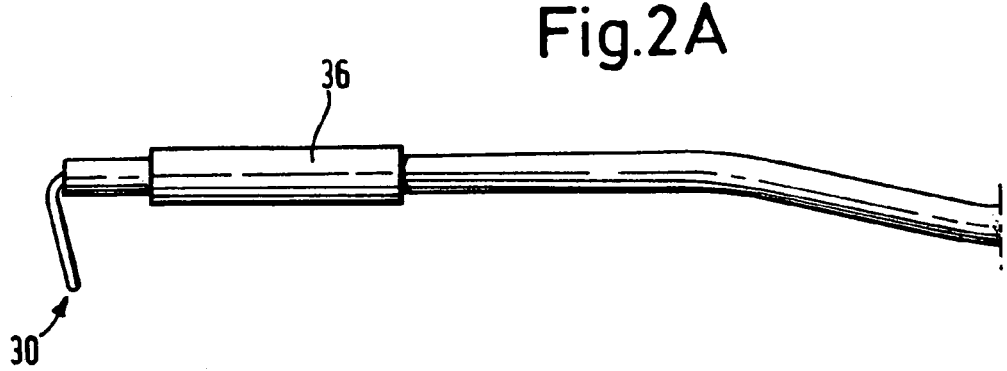
Fig.2A
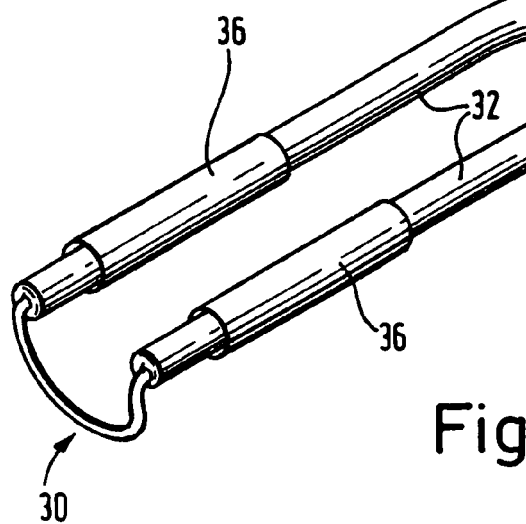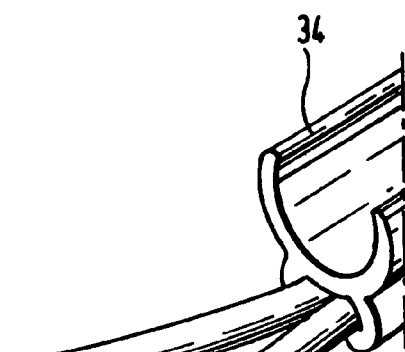
Fig.2B

ELECTROSURGICAL GENERATOR

This is a Continuation of application Ser. No. 10/743,095 filed Dec. 23, 2003 (now U.S. Pat. No. 7,211,081), which claims the benefit of U.S. Provisional Application No. 60/449,859 filed Feb. 27, 2003 and U.S. Provisional Application No. 60/505,756 filed Dec. 3, 2003. The disclosures of the prior applications are hereby incorporated by reference herein in their entirety.

FIELD OF THE INVENTION

This invention relates to an electrosurgical generator for supplying radio frequency (RF) power to an electrosurgical instrument, and primarily to a generator having a series-resonant output network.

BACKGROUND OF THE INVENTION

Conventionally, electrosurgical generators make use of a configuration comprising a voltage source coupled to an electrosurgical instrument via a coupling capacitor which defines a matched output impedance between 50 and 500 ohms. Such a configuration produces a power-versus-load impedance characteristic having a power maximum at a matched impedance, with power falling off progressively on each side of this peak. In practice, when conducting electrosurgery, the load impedance can change over a very wide range, resulting in unpredictable clinical effects.

To deal with this problem, it is known to provide an RF output stage capable of providing an impedance match over a wide range. This has the disadvantage that rapid load impedance changes can produce large output voltage excursions. An alternative approach is to control the DC supply to the RF output stage in response to feedback signals in order that the delivered power is virtually continuous. This may be done by adjusting the power supply DC voltage or by maintaining the supplied DC power constant. These techniques lead to a power versus load impedance characteristic which is virtually flat over a range of impedances, but one limitation is that it is difficult to control the delivery of energy when initiating tissue cutting or vaporisation (as opposed to tissue coagulation). To cut or vaporise tissue using radio frequency power, the initial low impedance load presented by the tissue or surrounding fluid needs to be brought to a higher impedance in order to strike an arc. Delivering too much energy can result in burns adjacent the operative site, excessive smoke, or instrument failure. Delivering too little energy causes a significant delay and can result in unwanted tissue coagulation.

It is also known to use an electrosurgical generator to supply a bipolar electrosurgical instrument with pulsed electrosurgical power at very high voltages, e.g. in the region of 1 kilovolt peak-to-peak when removing tissue at an operation site immersed in a conductive liquid, such as saline. The instrument may have an active electrode located at its extreme end to be brought adjacent to or into contact with tissue to be treated, and a return electrode set back from the active electrode and having a fluid contact surface for making an electrical connection with the conductive liquid. To achieve tissue removal, the conductive liquid surrounding the active electrode is vaporised to cause arcing at the electrode. The high voltages used to achieve tissue cutting or vaporisation under varying load impedance conditions are particularly demanding of the generator when the instrument experiences a low load impedance. Indeed, as stated above, under such conditions it is difficult reliably to initiate arcing without unwanted effects. Steps have been taken to increase power density at the active electrode and, hence, improve the reliability with which arcing is started, by reducing the size of the electrode and by roughening its surface, e.g. by applying an oxide layer. The latter technique has the effect of trapping vapour in the irregularities in the surface as a means of increasing power density.

It has been found that operation of such instruments at high voltages tends to cause erosion of the active electrode. The rate of erosion increases as the supply voltage is increased, and is also exacerbated by reducing the size of the electrode and providing a roughened surface, as just mentioned.

Published European Patent Application No. EP1053720A1 discloses a generator for generating high electrosurgical voltages.

SUMMARY OF THE INVENTION

According to a first aspect of the present invention, an electrosurgical generator for supplying RF power to an electrosurgical instrument comprises an RF output stage having a least one RF power device, at least one pair of output lines for delivering RF power to the instrument, and a series-resonant output network coupled between the RF power device and the said pair of output lines, wherein the output impedance of the output stage at the output lines is less than $200/\sqrt{P}$ ohms, where P is the maximum continuous RF output power of the generator in watts. When the generator is configured for wet field surgery, e.g. for use with the electrode or electrodes of the instrument immersed in a conductive fluid such as saline, the maximum continuous power is preferably in the region of 300 W to 400 W. Accordingly, if the maximum output power is 400 W, the output impedance is less than 10 ohms. Dry field electrosurgery, i.e. with the electrode or electrodes not normally immersed, requires less RF output power. In this case, the generator may be configured such that the maximum continuous RF output power is in the region of 16 W, in which case that the output impedance is then less than 50 ohms. In both such cases, the figures are obtained when operating with an output voltage for cutting or vaporising tissue, i.e. at least 300V peak. The output impedance is preferably less than $100/\sqrt{P}$ ohms, which yields maximum output impedance values of 5 ohms and 25 ohms at the above power outputs.

It will be understood that when the RF output of the generator is pulsed, i.e. when RF energy is supplied to a load in bursts, generally as an RF sine wave, the maximum continuous power is the average power measured over several such bursts.

According to another aspect of the invention, an electrosurgical generator for supplying RF power to an electrosurgical instrument for cutting or vaporising tissue comprises an RF output stage having: at least one RF power device, at least one pair of output lines for delivering RF power to the instrument, and a series-resonant output network coupled between the RF power device and the said pair of output lines, the network being configured such that the maximum rate of rise of the output current at the output lines is less than $(\sqrt{P})/4$ amps per microsecond, P being as defined above.

Accordingly, for a typical maximum continuous RF output power of 400 W for wet field electrosurgery, the maximum rate of rise of the output current amplitude, generally when the output lines are short-circuited at the maximum power setting of the generator, is less than 5 A/µs. With P at a typical value of 16 W for dry field electrosurgery, the rate of rise of the output current amplitude is less than 1 A/µs.

In a preferred generator in accordance with the invention, there is protection circuitry responsive to a predetermined electrical condition indicative of an output current overload, e.g. due to short-circuiting of the output lines, substantially to interrupt the RF power supplied to the series-resonant output network. The protection circuitry is responsive to short-circuiting with sufficient speed that the supply of RF power to the output network is cut off within a time period corresponding to no more than 20 cycles of the delivered RF power. The protection circuitry is preferably much faster, e.g. being operable to interrupt power delivery within 3 cycles or even 1 cycle. The effect of the series-resonant output network is to delay the build up of current in a fault condition such as when a very low impedance or a short circuit appears across the output lines. The applicants have found that an impedance transition from open to short circuit results in an effective short circuit across the RF power device only after several RF cycles. By arranging for the protection circuitry to respond quickly, the output stage can be disabled before that happens. In general, the protection circuitry is responsive to application of a short-circuit across the output lines sufficiently quickly to disable the RF power device before the current passing therethrough rises to a rated maximum current as a result of the short-circuit.

The use of an RF output stage with a relatively low output impedance means that the RF voltage output is substantially directly related to the DC supply voltage applied to the output stage (specifically to the RF power device or devices which it contains). In the preferred embodiment of the invention, each RF power device is operated in a switching mode with the result that a square wave output is applied to the series-resonant output network. The RMS voltage available at the output lines is directly proportional to the supply voltage. It follows that the maximum peak-to-peak output voltage is determined by the DC supply voltage and dynamic feedback to control output voltage is, as a result, not required in this embodiment.

The protection circuitry is preferably capable of disabling the output stage within one-and-a-half RF periods after onset of the above-mentioned predetermined electrical condition. Preferably, the predetermined electrical condition is indicative of an instantaneous current in the output stage exceeding a predetermined level, and the speed of response of the protection circuitry is such that the breaching of the predetermined level by the instantaneous current is detected during the same RF cycle that it occurs. Such detection may be performed by current sensing circuitry including a pick-up arrangement, which is typically a current transformer, coupled in series between the RF power device or devices and the series-resonant output network, and a comparator having a first input coupled to the pick-up arrangement (e.g. to the secondary winding of the transformer) and a second input coupled to a reference level source. The reference level source may be a voltage representation of the instantaneous current, i.e. substantially without filtering, in order to cause a change of state of the comparator output within the same RF half-cycle that the threshold is first exceeded, or within the subsequent half-cycle, depending on whether or not full wave rectification is applied ahead of the comparator. The predetermined instantaneous output level is preferably at least 5 A for wet field electrosurgery, and typically 15 A. The output of the comparator is coupled to disabling circuitry to disable the power device or devices when the comparator output changes state in response to the instantaneous current sensed by the pick-up arrangement exceeding the predetermined level as set by the reference source. The current shut-down aspect of the protection circuitry is not limited by impedance.

Generally, it is necessary only to interrupt power delivery for a short time. Consequently the protection circuitry includes a monostable stage and is operable in response to detection of the predetermined condition to disable the power device for a limited period determined by a time constant of the monostable stage which is typically less than 20 cycles of the operating frequency of the generator.

Preferably, the generator has an RF source coupled to the power device or devices, the source including an oscillator defining the operating frequency of the generator. The series resonant output network is tuned to this operating frequency. Generally, the source is arranged such that the operating frequency is substantially constant (e.g. during any given treatment cycle).

The preferred generator is arranged such that, for a given user setting, the RMS RF output voltage is substantially within a load impedance range of from $600/\sqrt{P}$ ohms to 1000 ohms, where P is as defined above. Thus, for instance, the RMS RF output voltage constant during each burst of RF energy is maintained to within 20 percent of a maximum value. This can be achieved partly as a result of the series-resonant configuration of the output network.

To maintain the constant peak output voltage at low impedances, according to a particular preferred feature of the invention, the RF power supply to the output stage includes a charge-storing element, preferably a capacitance in excess of 1 mF, the output devices being pulsed by a pulsing circuit so that they supply RF energy in bursts with the timing of the bursts, particularly the termination of each burst, being controlled in response to the output of a voltage sensing circuit coupled to the capacitance. The DC power supply voltage to the output stage is preferably 100V or greater. To avoid substantial decay of the supply voltage, the voltage sensing and pulsing circuits are arranged to terminate the individual pulses of RF energy when the sensed voltage falls below a predetermined level, typically set such that pulse termination occurs when the voltage falls by a predetermined percentage value of between 5 percent and 20 percent which, typically, corresponds to the peak RF voltage delivered at the output lines falling to a value between 25V and 100V below its starting value for the respective pulse. The RF energy delivered during each pulse is typically 60 joules for wet field electrosurgery and 2 joules for dry field electrosurgery. Peak power typically reaches at least 1 kW, and preferably 4 kW.

The very high peak power capability of the preferred wet field generator (in excess of 1 kW) allows the impedance transition occurring at the start of a tissue cutting or vaporisation cycle to be completed very quickly since only voltages in excess of those required for arcing are delivered. This significantly reduces the delay and the unwanted coagulation effects of some prior art generators. The substantially constant voltage delivery leads to cutting or vaporisation occurring at consistent rates, regardless of changes in tissue type or engagement.

According to a further aspect of the invention, there is provided an electrosurgical generator for supplying radio frequency (RF) power to an electrosurgical instrument, wherein the generator comprises an RF output stage having at least one RF power device, at least one pair of output lines for delivering RF power to the instrument, and a series-resonant output network coupled between the RF power device and the output lines, the generator further comprising protection circuitry responsive to a short circuit across the output lines, wherein the output impedance of the output stage is less than $200/\sqrt{P}$ ohms, where P is the maximum continuous RF output power of the generator in watts, and wherein the protection circuitry is responsive to the said short circuit sufficiently quickly to disable the power device before the current passing therethrough rises to a rated maximum current as a result of the short circuit. The or each power device may be disabled in response to application of the short-circuit to the output lines in a time period corresponding to less than three RF cycles.

Another aspect of the invention provides an electrosurgical generator for supplying radio frequency (RF) power to an electrosurgical instrument for cutting or vaporising tissue in wet field electrosurgery, wherein the generator comprises an RF output stage having: at least one RF power device, at least one pair of output lines for delivering RF power to the instrument, and a series-resonant output network coupled between the RF power device and the said pair of output lines, and wherein the output impedance of the output stage at the output lines is less than 10 ohms.

Yet another aspect of the invention provides an electrosurgical generator for supplying radio frequency (RF) power to an electrosurgical instrument for cutting or vaporising tissue in dry field electrosurgery, wherein the generator comprises an RF output stage having: at least one RF power device, at least one pair of output lines for delivering RF power to the instrument, and a series-resonant output network coupled between the RF power device and the said pair of output lines, and wherein the output impedance of the output stage at the output lines is less than 50 ohms.

According to a yet further aspect of the invention a generator for supplying RF power to an electrosurgical instrument for cutting or vaporising tissue comprises an RF output stage having: at least one RF power device, at least one pair of output lines for delivering RF power to the instrument, and a series-resonant output network coupled between the RF power device and the said pair of output lines, wherein the generator is configured to be capable of maintaining a peak output voltage of at least 300V over a load impedance range of from $600/\sqrt{P}$ ohms to 1000 ohms, where P is the rated output power in watts. The rated output power is as defined in the International Electrotechnical Commission standard, IEC 60601-2-2.

According to yet a further aspect of the invention, there is provided an electrosurgical generator for supplying RF power to an electrosurgical instrument for cutting or vaporising tissue, wherein the generator comprises an RF output stage having: at least one RF power device, at least one pair of output lines for delivering RF power to the instrument, and a series-resonant output network coupled between the RF power device and the said pair of output lines, wherein the generator further comprises a power supply stage coupled to the RF output stage, the power supply stage having an energy storage capacitor capable of storing between 3 percent and 30 percent of the maximum continuous power P (in watts) of the generator in joules.

In another aspect of the invention, the energy delivery per pulse (in joules) is between 1 percent and 10 percent of the maximum continuous RF output power (in watts).

The invention also includes an electrosurgical generator for supplying RF power to an electrosurgical instrument for cutting or vaporising tissue, wherein the generator comprises an RF output stage having: at least one RF power device, at least one pair of output lines for delivering RF power to the instrument, and a series-resonant output network coupled between the RF power device and the output lines, and wherein the generator further comprises a pulsing circuit coupled to the output stage for pulsing the delivered RF power in such a way that the crest factor of the voltage developed across the output lines increases as the load impedance presented to the output lines decreases whilst the peak output voltage during pulses is maintained at a value greater than 300V. For wet field electrosurgery, the output impedance of the output stage is preferably less than 10 ohms and the crest factor varies by a ratio of at least 2:1 over a load impedance range of from $600/\sqrt{P}$ to 1000 ohms (typically from 10 ohms to 1000 ohms). For dry field electrosurgery, the output impedance figure is less than 50 ohms, and the crest factor varies by a ratio of at least 2:1 over a load impedance range of $600/\sqrt{P}$ to 50 kilohms (typically from 50 ohms to 50 kilohms).

By "crest factor" we mean the ratio of the peak voltage to the RMS voltage. In the case of a pulsed output waveform, the measurement is conducted over plurality of pulses.

According to a tenth aspect of this invention, an electrosurgical generator comprises a source of radio frequency (RF) energy, an active output terminal, a return output terminal, a DC isolation capacitance between the source and the active output terminal, and a pulsing circuit for the source, wherein the source and the pulsing circuit are arranged to generate a pulsed RF output signal at the output terminals, which signal has a peak current of at least 1 A, a simultaneous peak voltage of at least 300V, a modulation rate of between 5 Hz and 2 kHz, and a pulse length of between 100 $\mu$s and 5 ms. In preferred embodiments of the invention, the signal has a peak current of at least 3 A.

With such a generator it is possible to start arcing even under conditions of relatively low load impedance. Once an arc is established, the load impedance tends to rise, to the extent that the arcing can be maintained using a continuous RF output waveform. Improved power density is available at the active electrode for vaporisation, whilst reducing electrode erosion.

The length of the pulses is preferably between 0.5 ms and 5 ms, the pulse duty cycle typically being between 1% and 20% and, more preferably, between 2% and 10%.

The preferred generator in accordance with the invention has a resonant output network and is operable to generate, e.g. during at least an initial part of a treatment period, a peak power of at least one kilowatt, and typically at least 3 or 4 kilowatts. Improvements in electrode erosion performance can be achieved by providing means in the generator for limiting the output voltage to a value in the region of 900V to 1100V peak-to-peak.

In the preferred generator, the source and the pulsing circuit are arranged to generate, in an initial period, a pulsed RF output signal at the output terminals, which signal has a peak current of at least 1 A, a simultaneous peak voltage of at least 300V, a modulation rate of between 5 Hz and 2 kHz, and a pulse length of between 100 $\mu$s and 5 ms, and, in a subsequent period, to generate a constant power RF output signal at the output terminals.

Different ways of causing the generator to end the above-mentioned initial period of operation and begin the so-called subsequent period are feasible. One generator embodiment is arranged such that the switchover from the initial period to the subsequent period occurs automatically at a predetermined time interval after the beginning of the initial period. In an alternative embodiment, the generator has means for monitoring, in use of the generator, the load impedance between the active and return output terminals, and is arranged to cause switchover to the subsequent period when the magnitude of the output impedance increases by a predetermined factor, typically between 5 and 20, and preferably 10, or when it exceeds a predefined threshold.

The preferred generator uses a third switching-over technique involving the charge-storing element mentioned above. In this case, the source of RF energy includes an RF output stage, and the generator has a power supply including the charge-storing element such as a large capacitor for supplying power to the output stage. When the treatment period includes an initial period and a subsequent period, as described above, the capacitor is used to supply power at least during the initial period. Associated with the charge-storing element is a voltage-sensing circuit for sensing the voltage supplied to the output stage by the charge-storing element, the generator being arranged such that treatment ends or the subsequent period begins in response to the supply voltage as sensed by the voltage-sensing circuit reaching a predetermined voltage threshold. Indeed, it is possible to control the length and timing of individual pulses using the same voltage-sensing circuit. In this case, the voltage-sensing circuit forms part of the above-mentioned pulsing circuit and the timing of at least the beginnings of the pulses produced by the output stage during the initial period being determined in response to the supply voltage reaching the above-mentioned voltage threshold. It is possible to arrange for both the leading and trailing edges of the pulses produced by the output stage to be determined by the supply voltage respectively falling below and exceeding the respective voltage thresholds.

The charge-storing capacitance is preferably at least 1000 μF and advantageously has a capacity in excess of 5 J.

As already stated, the preferred generator has a tuned output. Indeed, good results have been obtained using a generator with a resonant output network, the load curve of the generator (i.e. the curve plotting delivered power versus load impedance) having a peak at a load impedance below 50 ohms. Delivery of peak power levels into low load impedances is aided by forming the output network as a series-resonant network comprising the series combination of an inductance and a capacitance, the output of the network being taken across the capacitance. The output may be taken to all output terminal of the generator via a coupling capacitor and, optionally, a step-up transformer from a node between the inductance and the capacitance of the series combination. Whilst it is possible, instead, to take the output from across the inductance, taking it across the capacitor has the advantage of reducing switching transients. As a further alternative, the generator may have its output terminals connected to the resonant output network so that, effectively, when a load is connected to the terminals it is connected as an impedance in series with the inductance and capacitance forming the resonant combination, e.g. between the inductance and the capacitance.

The resonant output network typically provides a source impedance at the output terminals in the range of from 50 ohms to 500 ohms.

Not least because the resonant frequency of the output network can vary with load impedance as a result of coupling capacitance, the RF source may include a variable frequency RF oscillator, the output frequency advantageously being limited to a maximum value below the resonant frequency of the output network when connected to a matching load impedance, i.e. a load impedance equal to its source impedance.

The generator may be combined with a bipolar electrosurgical instrument to form an electrosurgical system, the instrument having at least an active electrode coupled to the active output terminal of the generator and a return electrode coupled to a generator return output terminal. The invention has particular application to an electrosurgery system in which the bipolar electrosurgical instrument has an active electrode formed as a conductive, preferably U-shaped loop. Such a loop is often used for excising tissue samples but places particular demands on the generator in terms of achieving saline vaporisation and arcing.

According to an eleventh aspect of the invention, an electrosurgery system comprises a generator having a source of radio frequency (RF) energy and, coupled to the generator, a bipolar electrosurgical instrument having an electrode assembly with at least a pair of electrodes, wherein the generator is adapted to deliver RF energy to the electrode assembly in an initial period as a pulse modulated RF signal which, in use with the pair of electrodes, has a peak current of at least 1 A, a simultaneous peak voltage of at least 300V, a modulation rate of between 5 Hz and 2 kHz, and a pulse length of between 100ȝs and 5 ms.

Again, the system may be adapted to deliver RF energy to the electrode assembly, in an initial period, as a pulse modulated RF signal which, in use with the pair of electrodes, has a peak current of at least 1 A, a simultaneous peak voltage of at least 300V, a modulation rate of between 5 Hz and 2 kHz, and a pulse length of between 100 μs and 5 ms, and to deliver RF energy to the electrode assembly in a subsequent period as a continuous power RF signal. The peak current is preferably at least 3 A.

The invention will be described below by way of example with reference to the drawings.

BRIEF DESCRIPTION OF THE DRAWINGS

In the drawings:

FIG. 1 is a general diagram showing an electrosurgery system including a generator in accordance with the invention and a bipolar electrosurgical instrument;

FIGS. 2A and 2B are respectively perspective and side views of a loop electrode assembly forming part of the bipolar instrument shown in FIG. 1;

DETAILED DESCRIPTION OF THE PREFERRED EMBODIMENTS

Figure 3:
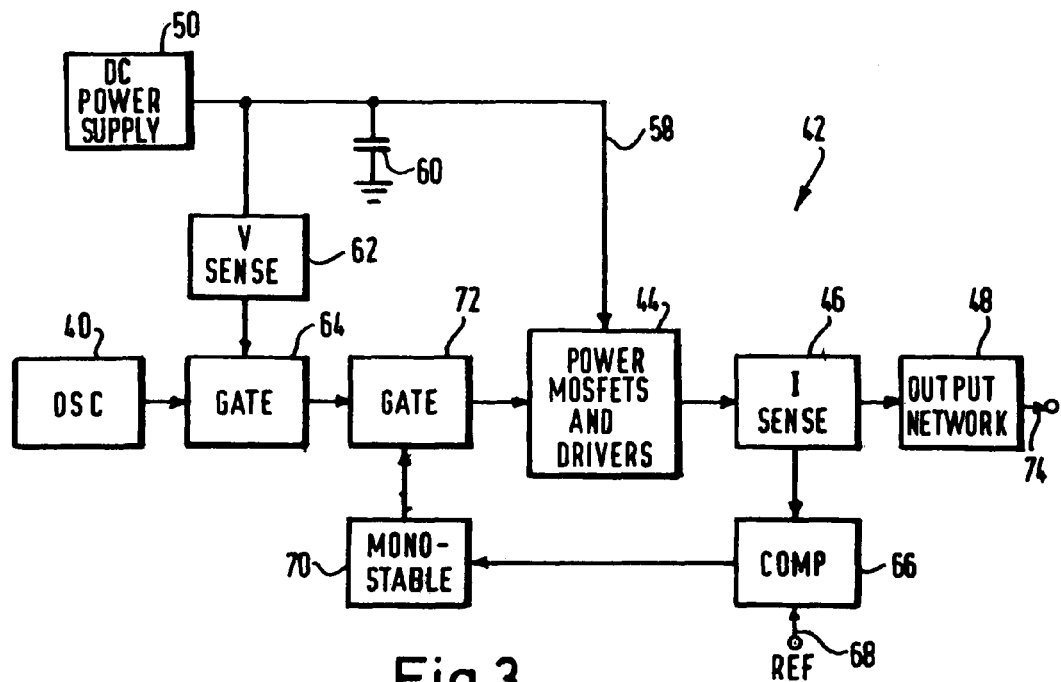
FIG. 3 is a block diagram illustrating the main components of the generator.

Referring to FIG. 1, a generator 10 has an output socket 10S providing a radio frequency (RF) output for an electrosurgical instrument in the form of an endoscope attachment 12 via a connection cord 14. Activation of the generator may be performed from the instrument 12 via a control connection in cord 14 or by means of a footswitch unit 16, as shown, connected separately to the rear of the generator 10 by a footswitch connection cord 18. In the illustrated embodiment, the footswitch unit 16 has two footswitches 16A and 18B for selecting a coagulation mode and a cutting mode of the generator respectively. The generator front panel has push buttons 20 and 22 for respectively setting coagulation and cutting power levels, which are indicated in a display 24. Push buttons 26 are provided as alternative means for selection between coagulation and cutting modes. The instrument 12 has a detachable loop electrode assembly 28 with a dual electrode structure and is intended for use in a saline field.

The instrument 12 has a detachable loop electrode assembly 28 with a dual electrode structure and intended for use in a saline field. FIGS. 2A and 2B are enlarged views of the distal end of the electrode assembly 28. At its extreme distal end the assembly has a U-shaped loop electrode 30 depending from a pair of electrode assembly arms 32 which are mounted side-by-side in a clip 34 intended to be snapped onto an endoscope. The loop electrode 30 is an active electrode. Each of the arms 32 is formed as a coaxial cable, the exposed conductive outer shield of which, in each case, forms a return electrode 36. In operation immersed in a saline field, the loop electrode 30 is typically used for excising tissue samples, the electrosurgical voltage developed between the loop electrode 12A and fluid contacting surfaces of the return electrodes 36 promoting vaporisation of the surrounding saline liquid at the loop electrode 30, and arcing through the vapour envelope so formed.

The loop electrode 30 comprises a composite molybdenum rhenium wire with an oxide coating to promote increased impedance in the electrode/fluid interface and, as a result, to increase power density at the surface of the electrode.

The width of the loop is typically in the range of 2.5 mm to 4 mm and the wire typically has a diameter in the range of 0.20 to 0.35 mm.

This loop electrode assembly places particular demands on the generator in terms of starting vaporisation and arc formation.

Efforts to improve the starting of the arc (the "firing up") of this electrode assembly by reducing the wire diameter and forming oxide layers have tended to increase the rate of erosion or resulted in the loop being mechanically flimsy.

It should be noted that generators in accordance with the invention not limited to use with a loop electrode assembly, nor to use in wet field surgery.

The generator will now be described in more detail with reference to FIG. 3. It has an RF source in the form of an oscillator 40 which is connectible to an RF output stage 42. The output stage 42 comprises a mosfet power bridge forming part of a power mosfet and driver circuit 44, a current sensing element 46 and a resonant output network 48. The oscillator 40 is configured to operate at a substantially constant RF frequency and the output network 48 is tuned to that frequency. In general terms, the RF source coupled to the RF power device or devices defines the operating frequency of the generator, and the output network (which, as will be described below, is series-resonant) is tuned to the operating frequency. In this embodiment of the invention the operating frequency is substantially constant.

Power to the RF output stage 42, or, more specifically, to the power mosfets, is supplied from a DC power supply 50 via a supply rail 58. A 4.7 mF reservoir capacitor 60 is connected between the supply rail 58 and ground. The voltage on the supply rail 58 is sensed by a voltage sensing circuit 62 which controls a first transmission gate 64 connected in series between the RF oscillator 40 and driver devices in the power mosfet and driver circuit 44.

The current sensing element 46 in the output stage 42 is a series-connected current transformer, the secondary winding of which is coupled to a first input of a comparator 66 which also receives on the other of its inputs a reference signal from a reference input 68. The output of the comparator controls a monostable 70 which, in turn, controls a second transmission gate 72 coupled in series with the gate 64 in the path between the oscillator 40 and the drivers in the power mosfet and driver circuit 44. The output network 48 supplies RF power to an output termination 74 which, in practice, is a pair of output lines, as will be described hereinafter. Operation of the generator is normally pulsed insofar as RF energy is supplied to the output lines 74 in bursts controlled by the combination of the voltage sensing circuit 62 and gate 64 which operates as part of a pulsing circuit. When the generator is activated, the voltage on the supply rail 58 tends to fall, at least when the load impedance coupled across output lines 74 is relatively low, owing to the discharge of reservoir capacitor 60. When the DC supply voltage on the supply rail 58 falls to a preset value, the output of the voltage sensing circuit 62 changes state and transmission gate 64 is driven to its open circuit condition, thereby disabling the power mosfet and driver circuit 44. The reservoir capacitor 60 then recharges and the voltage sensing circuit 62 causes the gate 64 to reconnect the oscillator 40 when the supply rail voltage reaches a second, higher present value. In this way it is possible to control the amount of energy delivered in each pulse.

The current sensing element 46, the comparator 66, the monostable 70 and the second transmission gate 72 act together as a protection circuit to protect the mosfet power devices in circuit 44 against excessive current drain caused, for instance, by a short circuit across the output lines 74. The storage of energy in output network 48 delays the transfer of the short circuit across the output lines 74 to the power devices in the mosfet and driver circuit 44.

The electrical circuit condition sensed by the current sensing element 46 and the comparator 66 is the current flowing between the power mosfets in circuit 44 and the output network 48 rising to a level which could be indicative of a short circuit having been applied across the output lines 74. When the current reaches a preset current level, as detected by the comparator 66, the comparator output changes state and the monostable 70 causes the second transmission gate 72 to become open circuit, disabling the power mosfets and driver stage 44. The monostable time constant is typically set to 0.5 seconds or less, which allows a warning signal to be generated for alerting the user. However, owing to energy storage in the series-resonant circuit, it is possible to protect the RF power devices with a monostable time constant of about 20 RF cycles at an operating frequency of 400 kHz.

Figure 4:
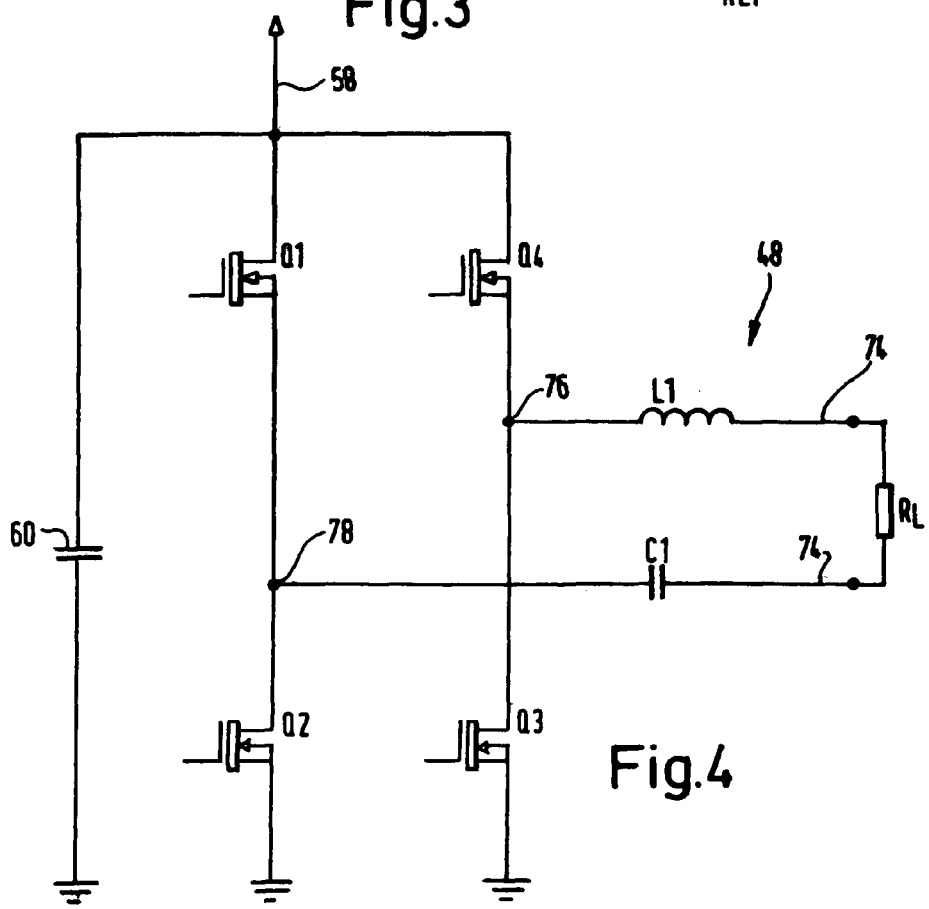
FIG. 4 is a simplified circuit diagram of an RF output stage forming part of the generator.

The configuration of the output stage 42 is shown in principle in the simplified circuit diagram of FIG. 4. Referring to FIG. 4, the power mosfet and driver stage 44 shown in FIG. 3 has a power mosfet bridge comprising a first push-pull pair of FET power devices Q1, Q2 and a second power FET device push-pull pair Q3, Q4, each pair having a respective output node which, when the pairs are driven 180° out of phase, produces a square wave at the frequency of the oscillator 40 (FIG. 2) at the input to the series resonant output network 48. Each pair of power mosfets Q1, Q2; Q3, Q4 is coupled between the supply rail 58 and ground. Accordingly, since each of the mosfets is a virtual short circuit when driven "on", the voltage applied to the output network 48 swings virtually between ground and the supply rail voltages. The reservoir capacitor 60 shown in FIG. 3 is, of course, connected across the respective power mosfet pairs, as shown in FIG. 4.

The output network is series-resonant in that an inductor L1 and a resonating capacitor C1 are coupled in series between the output nodes 76, 78 of the first and second power mosfet pairs respectively. In this embodiment, the load resistance $R_L$ constituted in practice by an electrosurgical instrument coupled between the output lines 74, and the tissue and/or fluid present across its electrode assembly, is connected in series between inductor L1 and capacitor C1. As explained above, the series-resonant tuned circuit formed by inductor L1 and capacitor C1 acts as an energy storing device which delays the current build-up between the nodes of the power mosfet bridge Q1-Q4 should the load resistance $R_L$ drop to a very low value. Another feature of this resonant arrangement is that it is a low impedance at one frequency only, which means that the delivered output signal consists almost exclusively of the fundamental component of the waveform produced by the power mosfets, conditional, of course, upon the frequency of resonance of the network 48 being the same as that of the operating frequency of the oscillator stage 40 (FIG. 3).

Figure 5:
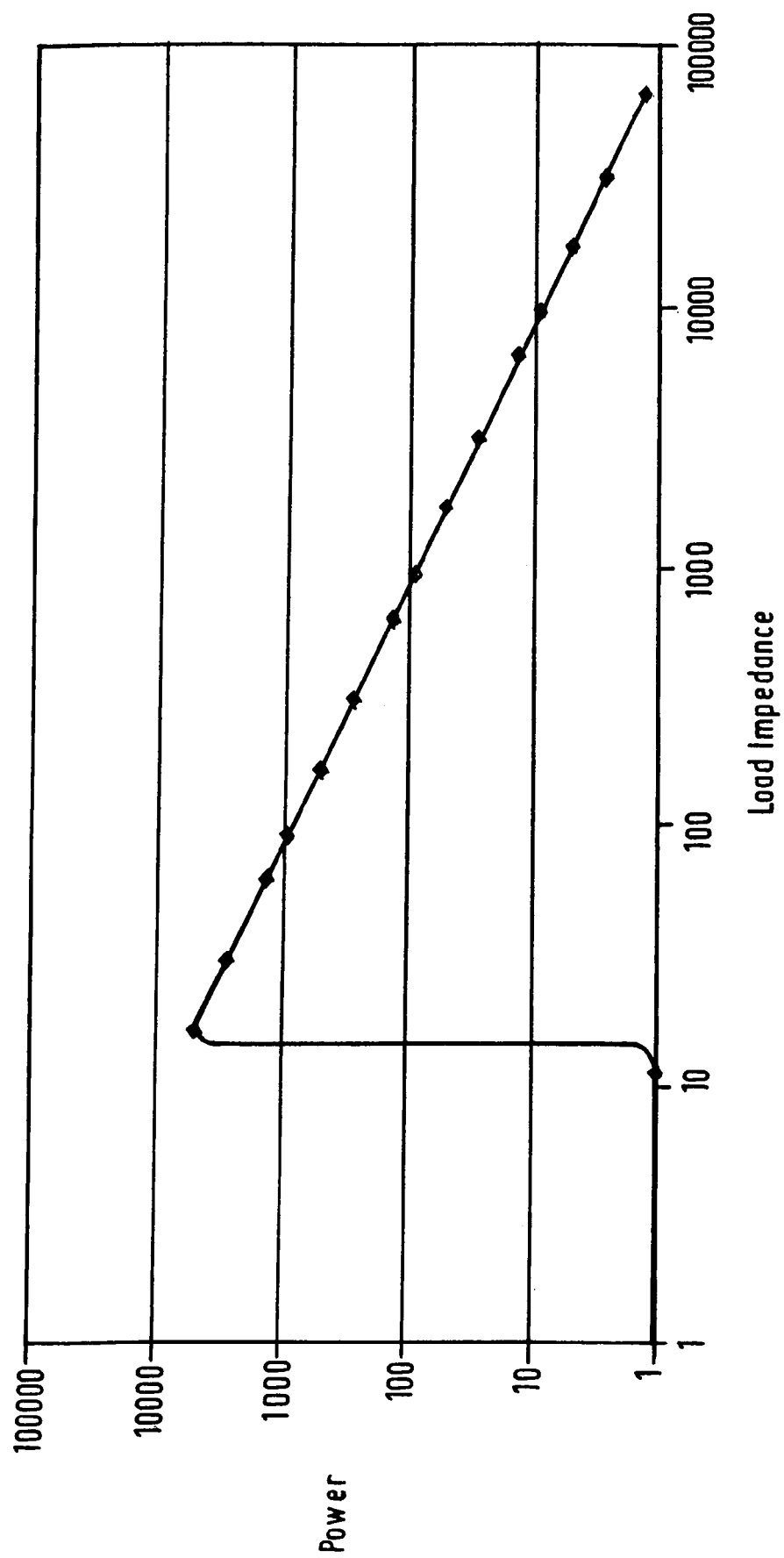
FIG. 5 is an illustrative load curve for the generator of FIG. 1.

One of the characteristics given to the generator by the output configuration described above with reference to FIG. 4 is that, during each burst or pulse of RF energy it has an approximately constant voltage load curve, as shown by the power-versus-load impedance load curve shown in FIG. 5. This characteristic is particularly suitable for cutting or vaporisation of tissue since it provides the high power required at low impedance without voltage overshoot. The low output impedance and high current required are provided by the direct coupling of the power mosfets to the supply rail and ground, and by the reservoir capacitor 60, even if a step-up transformer is coupled between the series-resonant elements L1, C1 and the output lines 74. It is possible, using this configuration, to keep the output impedance of the generator at the output lines 74 to 2 ohms or less. The implications which this has for peak current delivery in a fault condition leads to the need for a protection circuit such as that referred to above.

Figure 6:
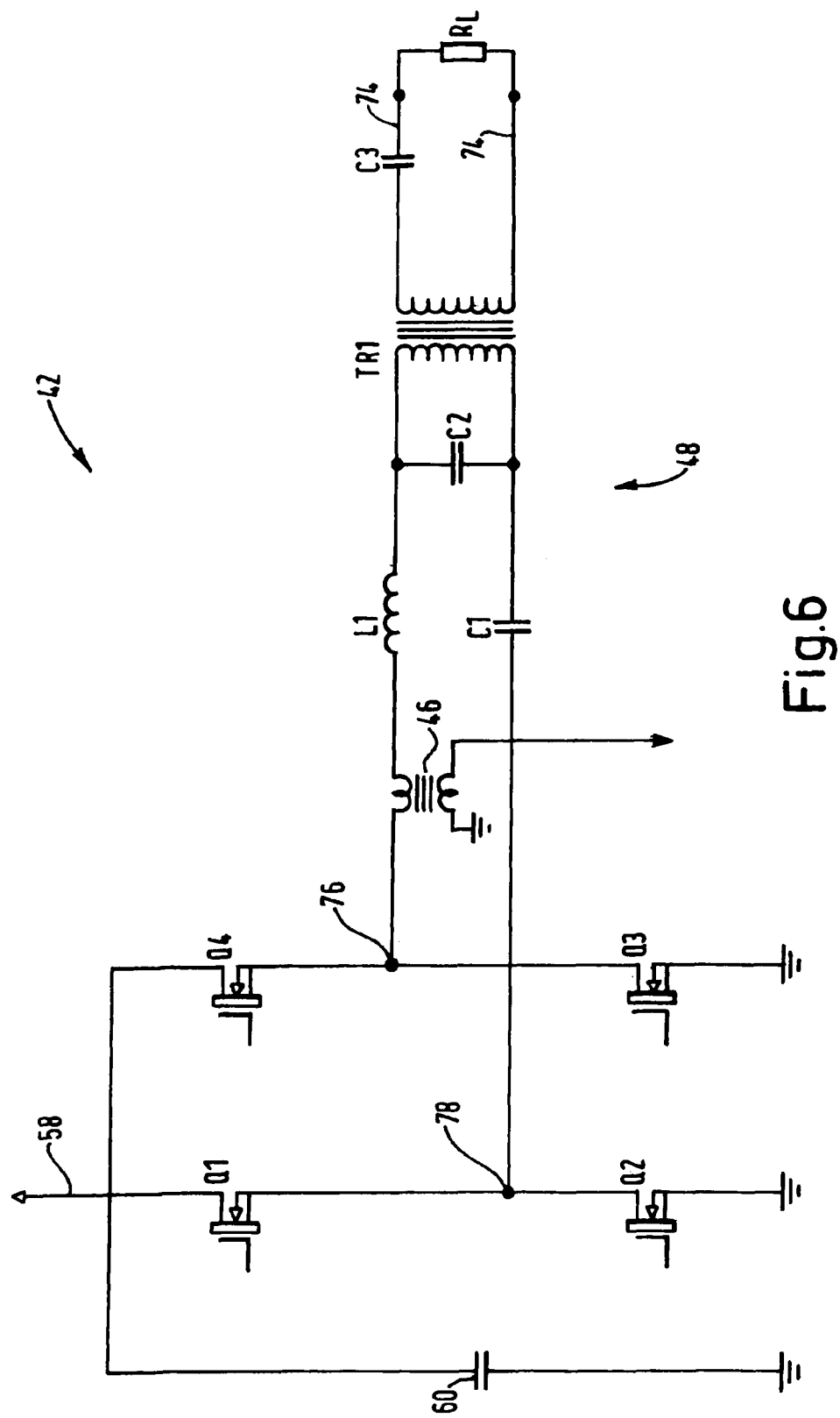
FIG. 6 is a more detailed circuit diagram of the RF output stage.

The RF output stage 42 is shown in more detail in FIG. 6. As shown in FIG. 6, the current sensing element 46 is a current transformer, coupled in series between one of the output nodes 76, 78 of the power mosfet bridge and one of the components L1, C1 of the series resonant output network, in this case between node 76 and the inductor L1. In this preferred generator, the normal DC supply voltage on supply rail 58 is about 120V. To strike an arc for the purpose of performing tissue cutting or vaporisation, a peak voltage in excess of 380V may be required. Accordingly, and for isolation purposes, the RF output network 48 includes a step-up isolating transformer TR1 to lift the peak output voltage to the region of 500V peak. The primary winding of the transformer TR1 has a tuning capacitor C2 coupled across it to yield a parallel-resonant circuit tuned to the operating frequency to act as a shunt-connected trap. This improves the rejection of harmonics in the power signal supplied to the output lines 74, particularly when the output impedance is high, with the consequent benefit of reduced RFI (RF interference).

DC blocking is provided by a coupling capacitor C3 between the transformer TR1 secondary winding and one of the output lines 74.

The actual resonant frequency of the output network 48 is the result of several elements, these being (1) the main tuning elements represented by the lumped inductance L1 and the tuning capacitor C1, (2) the transformer leakage inductance and cross-coupling capacitance, (3) the DC blocking capacitance, C3, and (4) the inductive and capacitive loading of the connecting cable (not shown) between the output lines 74 and the electrosurgical instrument itself. The delay in the current build-up in a fault condition is due to the energy levels in this tuned arrangement. At resonance, this arrangement has a finite loss that may be represented by a series resistance, albeit a very small one. Dynamically, however, the energy levels in the resonant output network cannot be changed instantly. An impedance transition from an open to short circuit only presents a short circuit to the switching stage after several RF cycles at the operating frequency. The comparator 66 shown in FIG. 3 is capable of detecting such an impedance transition within 1 to 1.5 cycles of the transition beginning at the output lines 74. This rapid response, as well as allowing the power mosfet and driver circuit 44 to be shut down before damage occurs, has the effect that the amount of energy delivered during a short circuit fault is very small.

Referring again to FIG. 3 and, in particular, the voltage sensing and output stage pulsing circuits 62, 64, the very high peak powers which are achievable with the output stage described above with reference to FIGS. 5 and 6 have the benefit that, during power delivery into a low impedance, the voltage across the reservoir capacitor 60 decreases progressively after the instant of generator activation. The capacitor value is chosen to be sufficiently large to ensure that the low to high load impedance transition occurring at the start of a tissue cutting or vaporisation cycle can be produced in a single burst of RF energy. Typically, the amount of energy delivered during the initial burst is about 1 joule in a dry environment and between 10 to 20 joules in a wet field environment. The actual energy in the RF pulses or bursts is controlled by the threshold or thresholds set in the voltage sensing circuit 62, specifically by the difference in supply voltage between pulse initiation and pulse termination. Since the output stage has a very low output impedance, this difference voltage is apparent as a change in delivered RF voltage at the output. The capacitor 60 is, therefore, made sufficiently large (in this embodiment 4.7 mF) that the change in voltage represents only a minor proportion of the absolute voltage at the output. Thus, if the delivered output voltage is a sine wave with a peak voltage of 500V, the supply voltage on supply rail 58, the size of the capacitor 60 and the transformer TR1 step-up ratio are chosen such that the output voltage drops by no more than 100V peak (20 percent) during an RF burst. In this preferred embodiment, the output voltage drop is about 50V peak or 10 percent.

One of the effects of preventing the supply of lower voltages to the output is that, in a tissue cutting or vaporisation tissue cycle, the voltage is not allowed to drop to a level at which undesirable coagulation effects occur.

The preferred generator in accordance with the present invention allows the DC energy fed to the reservoir capacitor 60 to be altered so that the time period during which a cutting voltage is present at the output can be altered. In practice, owing to the low output impedance of the generator, this time period is directly proportional to the stored energy.

The control methodology, whereby RF energy bursts or pulses are controlled according to voltage thresholds sensed across a reservoir capacitor, allows very low duty cycles to be used, permitting tissue cutting or vaporisation at low average powers. Indeed, it is possible to operate with less than 5 watts average power (averaged over several capacitor charging and discharging cycles). Accordingly, the generator has uses in low power as well as high power applications.

An alternative generator for use in the system described above with reference to FIG. 1 will now be described with reference to FIG. 7. This generator has a variable frequency RF source including a voltage controlled oscillator (VCO) 40A. In this example, the VCO feeds a divide-by-two stage 40B which, in turn, feeds a power driver stage 44A driving an RF output stage in the form of a power bridge 44B. The power bridge 44B feeds a resonant output network 80 which delivers a generator output signal across output terminals 74. In practice, the power driver stage 44A and the power bridge 44B can have the same configuration as the power mosfet and driver circuit 44 of the generator described above with reference to FIG. 3. The power bridge 44B takes its DC supply from the supply rail 58 of the DC power supply 50, but the driver stage 44A has a lower voltage supply. Typical supply voltages are 180V maximum for the power bridge 44B and 16.5V for the driver stage 44A.

To bring the frequency of the combination of the VCO 40A and divide-by-two stage 40B to the resonant frequency of the output network 80, the above-described components of the RF source are coupled in a phase-locked loop including a phase sensing element 82 coupled between the power bridge 44B and the output network 80 to sense the current phase in the input leads to the output network. This current phase signal is applied to one input of a phase comparator 84, the other input of which receives a signal representative of the output of the VCO 40A, derived from the output of the divide-by-two stage 40B via a delay stage 86 which compensates for the delay to the RF signal as it passes through the power driver and the power bridge.

As in the first-described generator, the RF output stage 44B is supplied from the DC supply rail 58 attached to the reservoir capacitor 60, which allows large currents to be drawn by the output stage 44B for short periods of time, i.e. currents significantly larger than the current rating of a power supply (not shown) connected to the DC supply rail 58. It follows that the voltage on supply rail 58 will fall during the time that a large current is drawn. Such variations in voltage are sensed by the voltage sensing stage 62 coupled to the rail 58. Voltage sensing circuit 62 has a control output coupled to the first transmission gate 64 in a line 88 coupling the divided-down output of the VCO 40A to the input of the power driver 44A.

As before, the arrangement of the voltage sensing stage 62 and the gate 64 are such that when the voltage on supply rail 58 (the voltage supplied to the power bridge 44B) drops below a predetermined voltage threshold, the gate 64 is operated to interrupt the signal path between the VCO and the power driver 44A. When the supply rail voltage rises again, the gate 64 reverts to its conducting state. This may happen when the voltage rises above the threshold mentioned above, or a second threshold voltage.

The second transmission gate 72, connected in series in the signal line 88 with the voltage-operated gate 64, has a control input connected to the output of a 0.5 second monostable 70 which is triggered by current sensing circuitry comprising the current sensing element 46 in one of the input leads to the output network 80 and the comparator 66. These elements act to interrupt the signal line 88 to the power driver 44A for 0.5 seconds when the power bridge output current exceeds a predetermined threshold.

Figure 8:
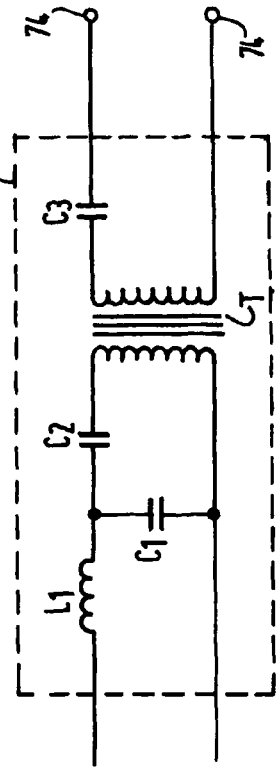
FIG. 8 is a circuit diagram of a resonant output network of the alternative generator.

Referring to FIG. 8, the resonant output network 80 comprises the series combination of an in-line inductance L and a tank capacitor $C_1$. The output is taken from across the tank capacitor $C_1$ (which takes out switching noise) via a first coupling capacitor $C_2$. This first coupling capacitor $C_2$ couples to the output (represented by terminals 74) via a step-up matching transformer T with a 1:2 step-up ratio. The secondary rewinding of the transformer T couples to the output terminals via a second coupling capacitor $C_3$. In this embodiment, L is about 0.473H, the tank capacitor is about 10 nF and the two coupling capacitors $C_2$ and $C_3$ co-operate (one of them via the transformer T) to form a coupling capacitance of about 23 nF.

It will be appreciated that when the output terminals 74 are open-circuit, the resonant frequency of the output network is determined by the series combination of L and $C_1$. When the output terminals 74 are shorted, the resonant frequency is determined by the series combination of L and the network represented by $C_1$, $C_2$, $C_3$ and T. With the values given, the short-circuit resonant frequency is about 0.55 times the open-circuit resonant frequency.

Figure 9:
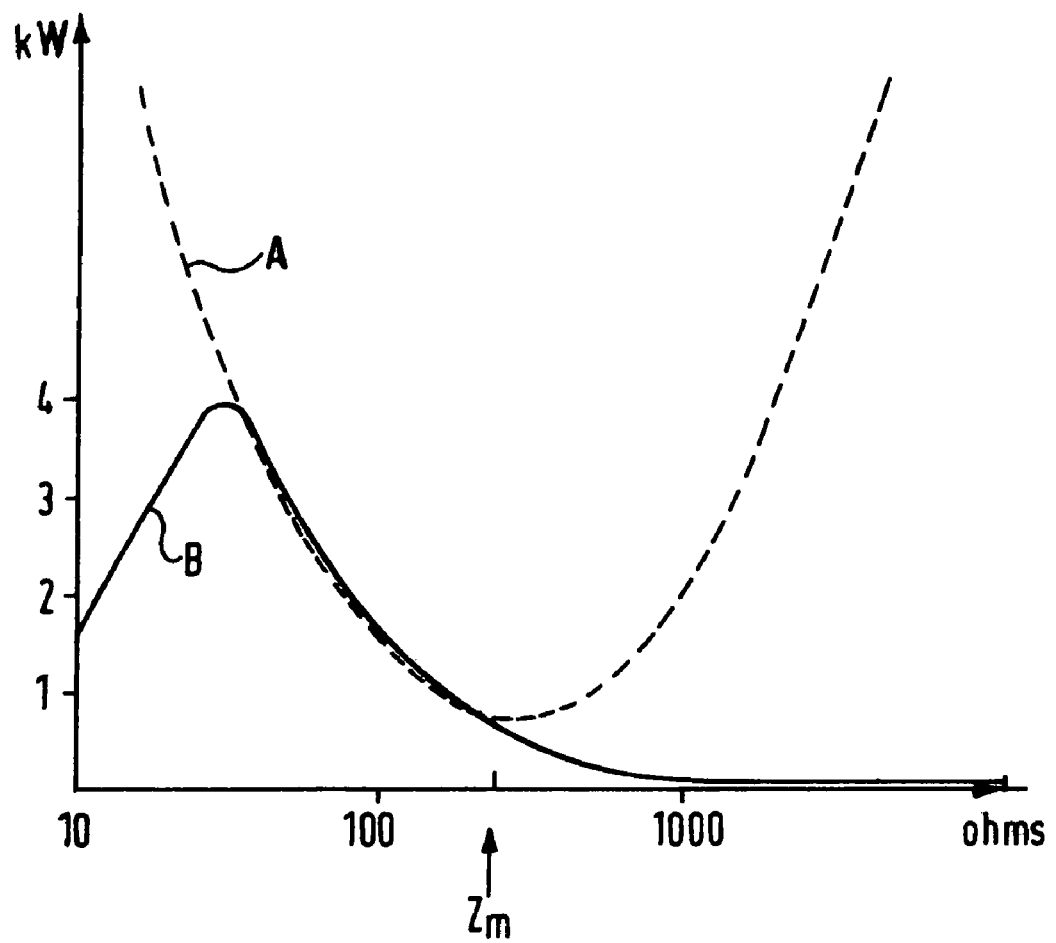
FIG. 9 is the load curve of the generator of FIG. 7.

One of the features of a series-tuned output stage is that peak power delivery inherently occurs at extremely low and extremely high impedances. Referring to FIG. 9, the load curve of a series-tuned network (i.e. the delivered power versus load impedance) at resonance is shown by the dotted curve A. The network 80 has minimum power delivery, which may be regarded as the "matched condition", at a load impedance across the terminals 74 (FIGS. 7 and 8) of about 200 ohms. It will be noted that the part of the curve A which has a negative slope follows a path which is approximately hyperbolic over a major part of its length, which means that this part of the curve is of similar shape to a constant voltage line on the graph of FIG. 9.

The applicant has recognised that such a characteristic, when applied to the output stage of an electrosurgical generator, allows output power to be maximised for a given constant voltage limit over a range of load impedances. It has been found that erosion of the active electrode of an electrosurgical instrument operated in a conductive liquid increases markedly when the output voltage rises above a threshold in the region of 900 volts to 1100 volts peak-to-peak. By arranging for the load curve of the output network 48 to follow an approximate constant voltage curve at about 1000 volts peak-to-peak (340 volts rms) the power delivered into a varying load impedance can be close to the maximum theoretically achievable for that voltage.

In effect, over the range of load impedances of importance in so-called "underwater" electrosurgery, the generator can be made to behave as a constant voltage supply. This can be achieved with a matched output impedance much higher than the load impedance presented by the electrode assembly shown in FIGS. 2A and 2B in the wetted condition, which, for a 4 mm loop is in the region of 25 ohms. This translates to a maximum power of about 4.5 kW at 340 volts rms.

Figure 7:
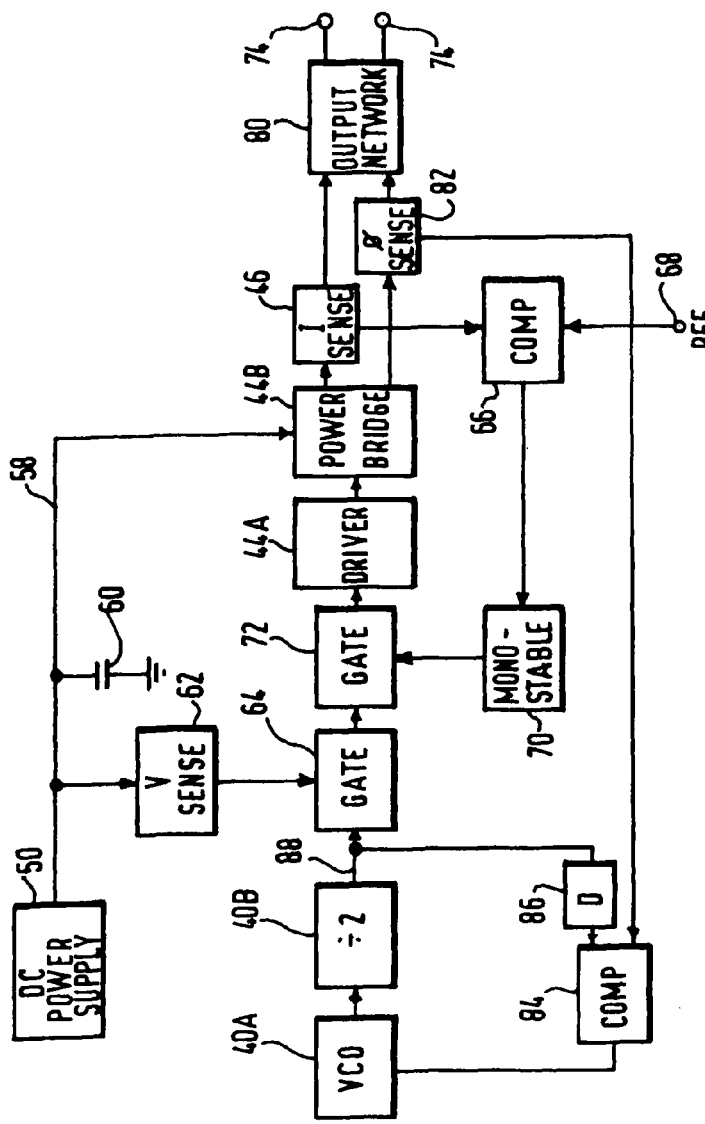
FIG. 7 is a block diagram of an alternative electrosurgical generator in accordance with the invention.

The actual load curve achieved with the arrangement shown in FIGS. 7 and 8 is shown by curve B in FIG. 9. This deviates from the series-tuned curve A at low impedances owing to imposition of a current limit using the current sensing stage circuitry 46, 66 monostable 70 and transmission gate 72 (FIG. 7). In the present embodiment, the current limit is set at a level of about 13 amps. The actual load curve B also deviates from the inherent series-tuned load curve A towards the lower part of the negative-slope portion of the curve A so that the delivered power follows a continuing negative gradient as the load impedance rises, again mimicking a constant voltage supply. This latter deviation is deliberate inasmuch as extreme power into a very high impedance is undesirable. The reason for this deviation is the movement of the resonant frequency of the output network 80, as described above, coupled with the imposition of a high-frequency limit on the RF frequency output as will be described below. The phase comparator 84 compares the current phase at the input to the output network 80, as sensed by the phase sensing circuit 82 with a delayed version of the output of the divide-by-two circuit 40B which, in turn, is fed by the VCO 40A. Accordingly, the phase and frequency of the VCO are varied to maintain a constant phase at the input to the output network 80, subject to the upper frequency limit mentioned above. In the absence of other influences, therefore, the output network 80 is maintained in resonance as the load impedance varies.

Given that the free-running frequency of the phase-locked loop is arranged to be its maximum frequency of operation, the locking characteristics of the phase-locked loop are such that it can be brought into a locked condition at the minimum frequency, corresponding to minimum load impedance, sufficiently quickly to achieve resonance in the early part of the output pulse, but not so quickly that the current limit circuit (sensing circuitry 46, 66 monostable 70 and gate 72) fails to trip when the current exceeds a predetermined current threshold.

If, now, the output carrier frequency is limited to a value below the frequency of the matched load resonant condition, the delivered power will fall off as the load impedance increases and the resonant frequency correspondingly rises. In fact, the free-run output frequency of the phase locked loop containing the VCO 40A (FIG. 7) is designed to be this maximum frequency. This ensures that the output network always represents a higher source impedance than the impedance of the load, which affords over-voltage protection in the event of a short.

Summarising, to achieve optimum resonant frequency, the excitation oscillator (VCO) is phase-locked to the resonant output network. Defining the range of the VCO provides load curve definition in that the delivered output power falls below the theoretical maximum when the output network resonant frequency rises above the maximum frequency of the divided down output of the VCO 40A. In other words, a match at high load impedance is prevented by preventing the VCO from generating the higher frequencies necessary for resonance. It also follows that, at high load impedances, the maximum output voltage is controlled by virtue of frequency.

It will be seen from FIG. 9 that the delivered output power is in excess of 1 kW over a range of load impedances corresponding to a wetted or partly wetted electrode. Once vaporisation and arcing has been initiated, the impedance rises, and the delivered power falls. To maintain the average output power at 200 W or less, the output signal is pulsed when the load impedance is low. It will be understood that with a peak power in excess of 4 kW, the pulse duty cycle needs to drop to a level in the region of 5% or less. The pulse repetition rate should be between 5 Hz and 2 kHz, and is preferably at least 10 Hz. These figures are chosen in view of the time taken to initiate vaporisation at the electrode surface. This means that the pulses have a maximum length of about 4 or 5 ms into a low impedance requiring maximum power. Typically, the pulse length is in the region of 1 to 2 ms. While it is not essential, configuring the RF output stage of the generator as an amplifier amplifying the output of a signal derived from a separate oscillator, rather than having a self-oscillating output stage, is preferred in order that full peak power can be achieved within the above-stated pulse lengths. (In this embodiment, the output stage 44B is an amplifier configured as a power switching bridge for high efficiency.) Should the VCO fail to operate at a frequency corresponding to resonance of the output network 80, as may happen at the start of each pulse, excessive output currents associated with such a mismatch are prevented since the series-tuned output network is low impedance only at resonance.

Pulsing of the output signal can be performed in a number of ways, including simply pulse modulating with predetermined pulse lengths and pulse repetition rates. In the mode of operation of the alternative generator described here, the output is pulsed only during an initial period from the commencement of treatment, the output signal being a continuous wave (CW) signal thereafter, i.e. generally when vaporisation and arcing have been achieved and the load impedance is in an upper range. The duration of the initial period may be fixed or it may be determined by monitoring the load impedance and terminating the initial period when the impedance exceeds a predetermined value. In this embodiment, the duration of the initial period and the length and frequency of the pulses are dynamically variable in response to delivered energy, as measured by the supply rail voltage on supply rail 58. As has been explained above, high instantaneous power levels are achieved only by allowing the output stage 44B to draw current from a charge reservoir, here a large capacitance such as capacitor the 47 mF capacitor 60. As charge is drawn from the capacitor 60, the supply rail voltage drops. Between pulses, the supply rail voltage rises again. Accordingly, by using gate 64 alternately to allow and prevent the passage of an RF signal along signal line 88 to the power driver 44A according to the relationship between the supply voltage level and a threshold or thresholds set in the voltage sensing circuit 62, the output of the generator can be pulsed to achieve maximum peak delivered power whilst operating within a predetermined average power limit. This equilibrium of power consumption and DC supply voltage is achieved by setting the voltage thresholds so that the RF output stage is activated when the supply rail voltage is sufficient to achieve a maximum vaporisation voltage (e.g. 340V rms) and switched off when a lower threshold is reached. The lower threshold defines the maximum energy per pulse and the repetition rate for a given average power level. The initial period referred to above is terminated when the electrode has "fired-up", in other words when vaporisation and arcing have commenced, so that the load impedance rises and the supply rail voltage stays above the switching threshold or thresholds. In this way it is possible to achieve vaporisation of the conductive liquid surrounding the electrode at impedances as low as 20 ohms without unacceptable erosion of the electrode surface.

What is claimed is:

1. An electrosurgical generator for supplying radio frequency (RF) power to an electrosurgical instrument for cutting or vaporising tissue, the generator comprising:
    an RF output stage having at least one RF power device, at least one pair of output lines for delivering RF power from the RF power device to the instrument, and a series-resonant output network coupled between the RF power device and the pair of output lines; and
    a power supply stage which is coupled to the RF output stage and includes:
        a charge-storing element for supplying power to each RF power device, the power supply stage being configured such that the charge-storing element is capable of storing charge in excess of 5 joules;
        a voltage-sensing circuit arranged to sense voltage supplied to the RF output stage by the charge-storing element; and
        a pulsing circuit coupled to the voltage sensing circuit for pulsing each RF power device;
    the arrangement of the voltage sensing and pulsing circuits being such that a timing of the pulses is varied in response to the sensed voltage.

2. A generator according to claim 1, wherein the power supply stage is configured such that the charge-storing element is capable of storing between 3% and 30% of the maximum continuous power P (in watts) of the generator in joules.

3. A generator according to claim 1, wherein the charge-storing element has a capacitance in excess of 1 mF.

4. A generator according to claim 1, wherein the pulsing circuit and the power supply stage are arranged to deliver pulses of RF energy to the output lines, the energy delivery per pulse (in joules) being between 1% and 10% of the maximum continuous RF output power (in joules).

5. A generator according to claim 1, wherein the voltage sensing circuit and the pulsing circuit are arranged to terminate individual pulses of RF energy delivered by each RF power device when the sensed voltage falls below a predetermined level.

6. A generator according to claim 5, wherein the predetermined level is set such that the pulse termination occurs when the sensed voltage falls by a predetermined percentage value of between 5% and 20%.

7. A generator according to claim 5, wherein the predetermined level is set such that, for each pulse, pulse termination occurs when a peak RF voltage delivered at the output lines has fallen to a value of between 25V and 100V below a starting value for the pulse.

8. A generator according to claim 1, wherein the power supply stage and the pulsing circuit are arranged to generate a pulsed RF output signal at the output lines, which signal has a peak current of at least 1 A, a simultaneous peak voltage of at least 300V, a modulation rate of between 5 Hz and 2 kHz, and a pulse length of between 100 μs and 5 ms.

9. A generator according to claim 8, wherein the pulse length is between 0.5 ms and 5 ms.

10. A generator according to claim 8, wherein a pulse duty cycle is between 1% and 20%.

11. A generator according to claim 8, wherein the simultaneous peak voltage is maintained throughout the entire pulse length.

12. An electrosurgical generator for supplying radio frequency (RF) power to an electrosurgical instrument for cutting or vaporising tissue, the generator comprising:
  an RF output stage having at least one RF power device and at least one pair of output lines for delivering RF power from the RF power device to the instrument;
  protection circuitry responsive to a predetermined electrical condition indicative of an output current overload to substantially interrupt the RF power supplied to the output lines; and
  a power supply stage which is coupled to the RF output stage and includes:
    a charge-storing element for supplying power to each RF power device, the power supply stage being configured such that the charge-storing element is capable of storing charge in excess of 5 joules;
    a voltage-sensing circuit arranged to sense voltage supplied to the RF output stage by the charge-storing element; and
    a pulsing circuit coupled to the voltage sensing circuit for pulsing each RF power device;
  the arrangement of the voltage sensing and pulsing circuits being such that a timing of the pulses is varied in response to the sensed voltage.

13. An electrosurgical generator for supplying radio frequency (RF) power to an electrosurgical instrument for cutting or vaporising tissue, the generator comprising:
  an RF output stage having at least one RF power device and at least one pair of output lines for delivering RF power from the RF power device to the instrument; and
  a power supply stage which is coupled to the RF output stage and includes:
    a charge-storing element for supplying power to each RF power device, the power supply stage being configured such that the charge-storing element is capable of storing charge in excess of 5 joules;
    a voltage-sensing circuit arranged to sense voltage supplied to the RF output stage by the charge-storing element; and
    a pulsing circuit coupled to the voltage sensing circuit for pulsing each RF power device;
  wherein:
    the arrangement of the voltage sensing and pulsing circuits being such that a timing of the pulses is varied in response to the sensed voltage;
    the generator is configured to supply RF power to the instrument for cutting or vaporising tissue in wet field electrosurgery; and
    an output impedance of the RF output stage at the output lines is less than 10 ohms.

14. An electrosurgical generator for supplying radio frequency (RF) power to an electrosurgical instrument for cutting or vaporising tissue, the generator comprising:
  an RF output stage having at least one RF power device and at least one pair of output lines for delivering RF power from the RF power device to the instrument; and
  a power supply stage which is coupled to the RF output stage and includes:
    a charge-storing element for supplying power to each RF power device, the power supply stage being configured such that the charge-storing element is capable of storing charge in excess of 5 joules;
    a voltage-sensing circuit arranged to sense voltage supplied to the RF output stage by the charge-storing element; and
    a pulsing circuit coupled to the voltage sensing circuit for pulsing each RF power device;
  wherein:
    the arrangement of the voltage sensing and pulsing circuits being such that a timing of the pulses is varied in response to the sensed voltage;
    the generator is configured to supply RF power to the instrument for cutting or vaporising tissue in dry field electrosurgery; and
    an output impedance of the RF output stage at the output lines is less than 50 ohms.

* * * * *